(12) United States Patent
Dacquay et al.

(10) Patent No.: US 7,811,252 B2
(45) Date of Patent: Oct. 12, 2010

(54) DOSAGE CONTROL DEVICE

(75) Inventors: Bruno Dacquay, Irvine, CA (US);
Cesario Dos Santos, Aliso Viejo, CA (US); Casey Lind, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 11/688,573

(22) Filed: Mar. 20, 2007

(65) Prior Publication Data

US 2007/0270760 A1    Nov. 22, 2007

Related U.S. Application Data

(63) Continuation-in-part of application No. 11/435,906, filed on May 17, 2006, now abandoned.

(60) Provisional application No. 60/921,497, filed on Oct. 16, 2006.

(51) Int. Cl.
*A61M 5/00* (2006.01)
(52) U.S. Cl. .................... 604/110; 128/DIG. 1
(58) Field of Classification Search ............... 604/110, 604/111, 113, 114, 93.01, 154, 232; 128/DIG. 1
See application file for complete search history.

(56) References Cited

U.S. PATENT DOCUMENTS

| | | | |
|---|---|---|---|
| 1,252,614 A * | 1/1918 | Pieper | ............ 392/476 |
| 3,892,537 A | 7/1975 | Gulati et al. | |
| 4,122,850 A | 10/1978 | Bucalo | |
| 4,265,618 A | 5/1981 | Herskovitz et al. | |
| 4,357,136 A | 11/1982 | Herskovitz et al. | |
| 4,392,827 A | 7/1983 | Martin | |
| 4,582,488 A | 4/1986 | Newman | |
| 4,684,344 A | 8/1987 | Brockway et al. | |
| 4,704,088 A | 11/1987 | Newman | |
| 4,992,045 A | 2/1991 | Beisel | |
| 4,996,477 A | 2/1991 | Keeler et al. | |
| 5,383,858 A * | 1/1995 | Reilly et al. | ............ 604/152 |
| 6,270,343 B1 | 8/2001 | Martin | |
| 6,364,865 B1 | 4/2002 | Lavi et al. | |
| 6,436,143 B1 | 8/2002 | Ross et al. | |
| 6,520,930 B2 * | 2/2003 | Critchlow et al. | ............ 604/67 |

(Continued)

FOREIGN PATENT DOCUMENTS

EP    0 348 146 A1    12/1989

(Continued)

*Primary Examiner*—Kevin C Sirmons
*Assistant Examiner*—Deanna K Hall
(74) *Attorney, Agent, or Firm*—Kenneth D. Bassinger (57) ABSTRACT

An injection device includes a dispensing chamber, a plunger, a controller, a memory device resistant to sterilization, and a housing at least partially enclosing the dispensing chamber and the plunger. The dispensing chamber has an inner surface and an outer surface. The inner surface defines a cavity for receiving a quantity of a substance. The plunger is engaged with the inner surface of the dispensing chamber, is capable of sliding in the cavity of the dispensing chamber, and is fluidly sealed to the inner surface of the dispensing chamber. The controller controls the operation of the injection device. The controller reads dosage data from the memory device and operates the injection device to deliver a dosage corresponding to the dosage data.

19 Claims, 6 Drawing Sheets

U.S. PATENT DOCUMENTS

| | | |
|---|---|---|
| 6,585,700 B1 | 7/2003 | Trocki et al. |
| 6,595,979 B1 | 7/2003 | Epstein et al. |
| 6,726,654 B2 | 4/2004 | Rosenman |
| 6,940,209 B2 | 9/2005 | Henderson |
| 6,991,457 B2 | 1/2006 | Kazen et al. |
| 7,176,030 B2 * | 2/2007 | Faries et al. .................... 436/1 |
| 2002/0055720 A1 | 5/2002 | Hohlfelder et al. |
| 2003/0055380 A1 | 3/2003 | Flaherty |
| 2004/0054319 A1 | 3/2004 | Langley et al. |
| 2004/0176720 A1 | 9/2004 | Kipfer |
| 2004/0231667 A1 | 11/2004 | Horton et al. |
| 2005/0065477 A1 | 3/2005 | Jost |
| 2005/0177137 A1 | 8/2005 | Kipfer |

FOREIGN PATENT DOCUMENTS

| | | |
|---|---|---|
| EP | 0398394 | 11/1990 |
| EP | 0 419 117 A2 | 3/1991 |
| GB | 1551767 | 8/1979 |
| WO | WO 82/03761 A1 | 11/1982 |
| WO | WO 87/00029 A1 | 1/1987 |
| WO | WO 93/02720 | 2/1993 |
| WO | WO 96/03978 A1 | 2/1996 |
| WO | WO 99/33853 A2 | 7/1999 |
| WO | WO 99/65548 | 12/1999 |
| WO | WO 01/10482 A1 | 2/2001 |

* cited by examiner

DOSAGE CONTROL DEVICE

RELATED APPLICATIONS

This application is a continuation-in-part of U.S. Provisional Patent Application No. 60/921,497, converted from U.S. patent application Ser. No. 11/581,629 filed Oct. 16, 2006, and which is a continuation-in-part of U.S. patent application Ser. No. 11/435,906 filed May 17, 2006, now abandoned.

BACKGROUND OF THE INVENTION

The present invention relates to a device for injecting a drug into an eye and more particularly to an ophthalmic drug delivery device with a dosage control mechanism.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

Figure 1:
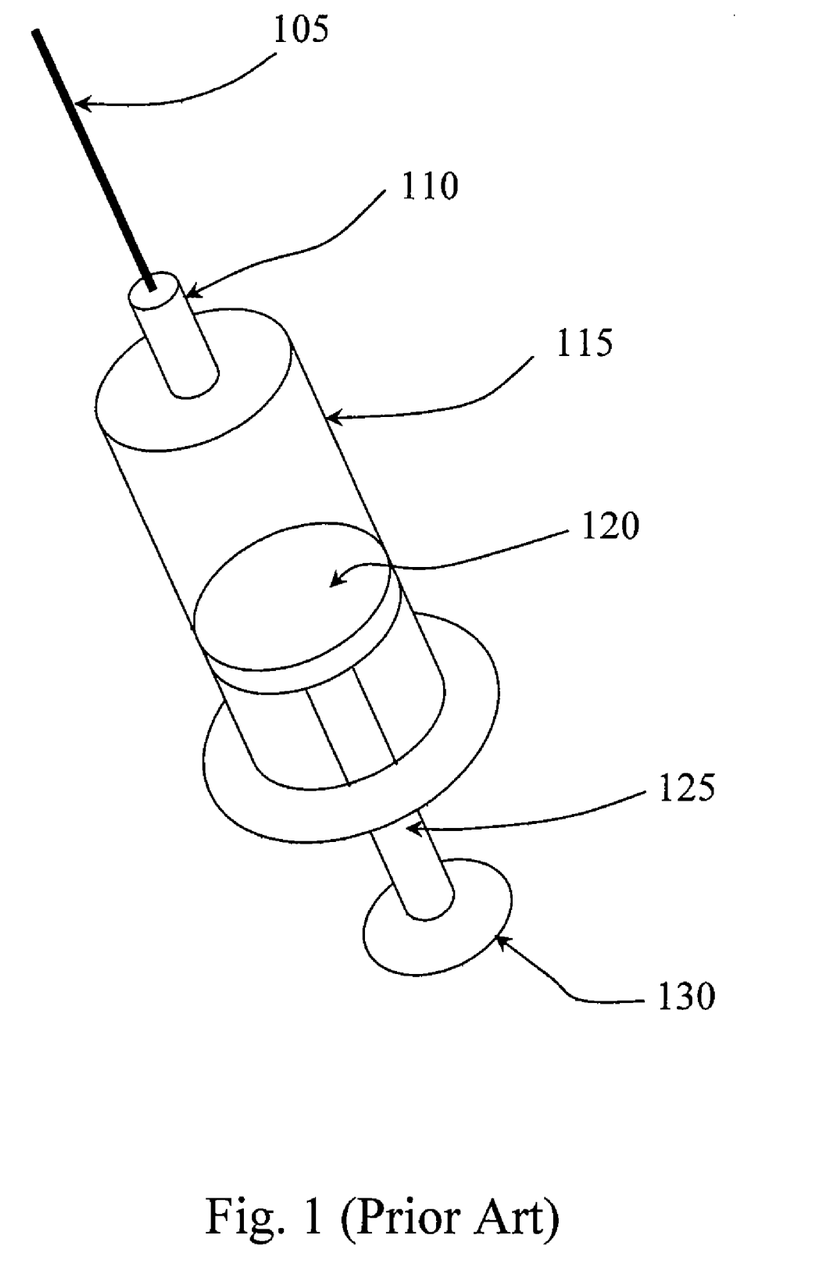
FIG. 1 is a perspective view of a prior art syringe.

These, and other diseases, can be treated by injecting a drug into the eye. Such injections are typically manually made using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to puncture the eye tissue with the needle, hold the syringe steady, and actuate the syringe plunger (with or without the help of a nurse) to inject the fluid into the eye. The volume injected is typically not controlled in an accurate manner because the vernier on the syringe is not precise relative to the small injection volume. Fluid flow rates are uncontrolled. Reading the vernier is also subject to parallax error. Tissue damage may occur due to an "unsteady" injection.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. With this type of dispenser, the volumes delivered are highly dependent on fluid viscosity, surface tension, and the specific dispensing tip. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. While precise, this dispenser is expensive and requires an electrical signal to be delivered to the dispensing mechanism.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a dosage control device for an ophthalmic injection system that assures that the correct dosage is delivered during each injection. Such a device would eliminate dosing error on the part of medical professionals during an injection and would be desirable for insuring accurate dosing during a clinical trial of a drug.

SUMMARY OF THE INVENTION

In one embodiment consistent with the principles of the present invention, the present invention is an injection device with a dispensing chamber, a plunger, a controller, a memory device resistant to sterilization, and a housing at least partially enclosing the dispensing chamber and the plunger. The dispensing chamber has an inner surface and an outer surface. The inner surface defines a cavity for receiving a quantity of a substance. The plunger is engaged with the inner surface of the dispensing chamber, is capable of sliding in the cavity of the dispensing chamber, and is fluidly sealed to the inner surface of the dispensing chamber. The controller controls the operation of the injection device. The controller reads dosage data from the memory device and operates the injection device to deliver a dosage corresponding to the dosage data.

In another embodiment consistent with the principles of the present invention, the present invention is an ophthalmic injection system having a tip segment and limited reuse assembly. The tip segment includes a dispensing chamber, a plunger, a memory device resistant to sterilization, and a housing at least partially enclosing the dispensing chamber and the plunger. The dispensing chamber has an inner surface and an outer surface. The inner surface defines a cavity for receiving a quantity of a substance. The plunger is engaged with the inner surface of the dispensing chamber, is capable of sliding in the cavity of the dispensing chamber, and is fluidly sealed to the inner surface of the dispensing chamber. The plunger has a proximate end with a first mechanical linkage interface. The controller controls the operation of the injection device. The limited reuse assembly includes a power source, a controller for controlling the operation of the system, a actuator with a shaft, a second mechanical linkage interface located on an end of the shaft, and a housing at least partially enclosing the controller and the actuator. The controller reads dosage data from the memory device and operates the injection device to deliver a dosage corresponding to the dosage data.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 2:
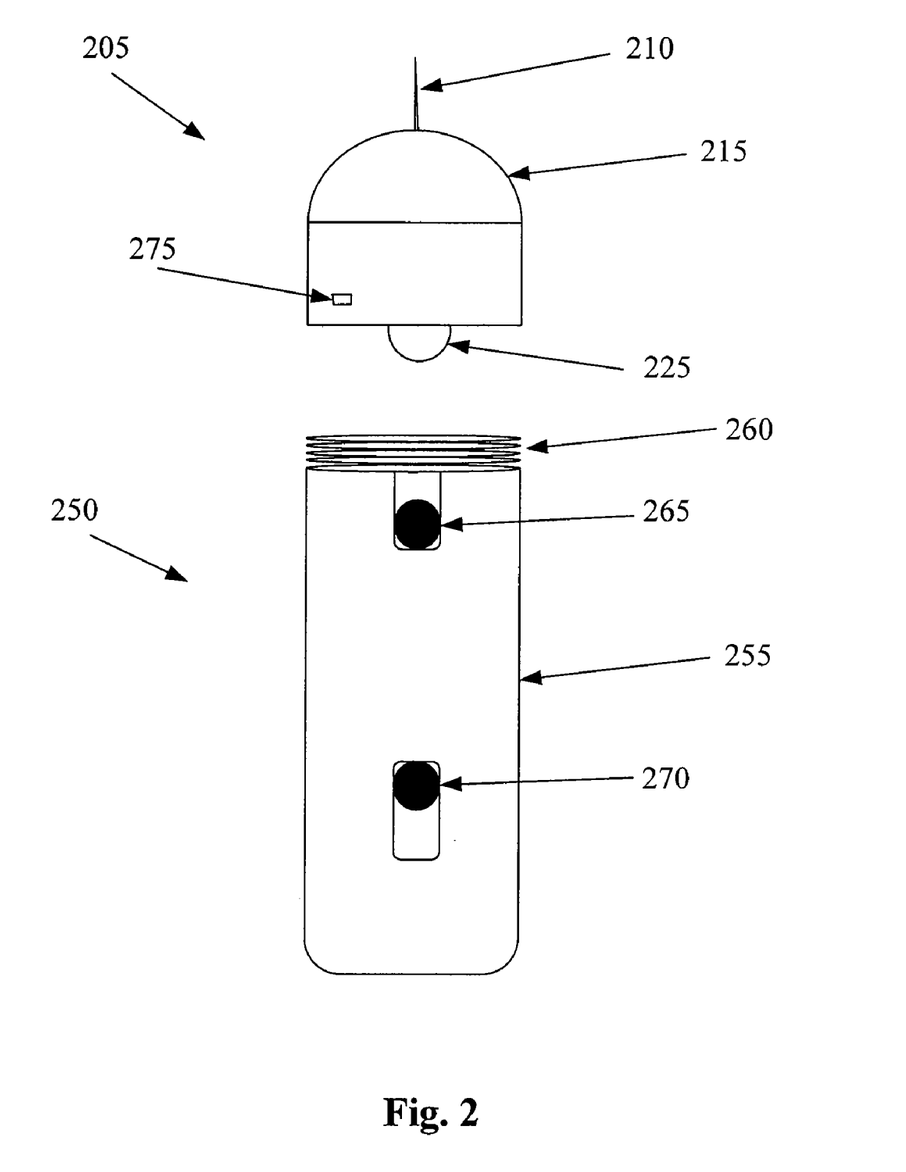
FIG. 2 is a view of an ophthalmic hand piece including a drug delivery tip segment and a limited reuse assembly according to an embodiment of the present invention.

FIG. 2 depicts one view of an ophthalmic hand piece including a drug delivery tip segment and a limited reuse assembly according to an embodiment of the present invention. In FIG. 2, the hand piece includes a tip segment 205 and a limited reuse assembly 250. The tip segment 205 includes a needle 210, a housing 215, a plunger connection 225, and an optional light 275. The limited reuse assembly 250 includes a housing 255, a switch 270, a lock mechanism 265, and a threaded portion 260.

Tip segment 205 is capable of being connected to and removed from Limited reuse assembly 250. In this embodiment, tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button, a sliding switch, or a cantilevered mechanism. Other mechanisms for connecting tip segment 205 to limited reuse assembly 250, such as those involving structural features that mate with each other, are commonly known in the art and are within the scope of the present invention.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length to facilitate proper delivery of the drug.

Switch 270 is adapted to provide an input to the system. For example, switch 270 may be used to activate the system or to turn on a heater. Other switches, buttons, or user-directed control inputs are commonly known and may be employed with limited reuse assembly 250 and/or tip segment 205.

Optional light 275 is illuminated when tip segment 205 is ready to be used. Optional light 275 may protrude from housing 215, or it may be contained within housing 215, in which case, optional light 275 may be seen through a clear portion of housing 215. In other embodiments, optional light 275 may be replaced by an indicator, such as a liquid crystal display, segmented display, or other device that indicates a status or condition of the tip segment. For example, optional light 275 may also pulse on and off to indicate other states such as but not limited to a system error, fully charged battery, insufficiently charged battery or faulty connection between the tip segment 205 and limited use assembly 250.

Figure 3:
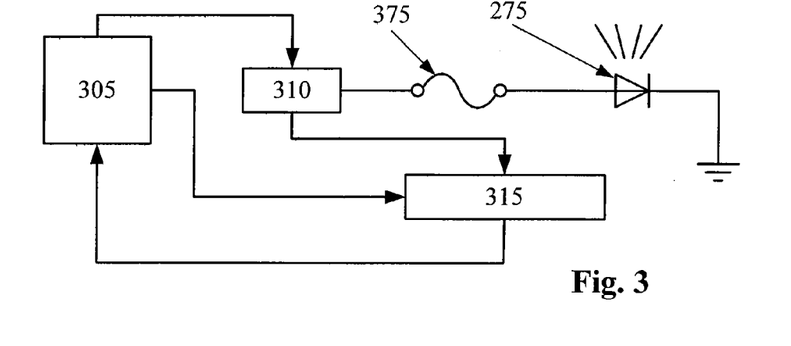
FIG. 3 is a diagram of a memory device circuit for use in a drug delivery tip segment according to an embodiment of the present invention.

FIG. 3 is a diagram of a memory device circuit for use in a drug delivery tip segment according to an embodiment of the present invention. In FIG. 3, the circuit includes optional light 275, fuse 375, controller 305, power source 310, and memory device 315. Controller 305 controls the operation of power source 310 and reads data stored on memory device 315.

In the embodiment of FIG. 3, optional light 275 is a light emitting diode of any appropriate color. In other embodiments, optional light 275 may be a lamp, a phosphorescent light, or any other similar electric or electronic light source. In other embodiments, optional light 275 is any type of indicator, such as a liquid crystal display or a segmented display.

Fuse 375 is a fuse with a current rating greater than the operating current of optional light 275. Fuse 375 may be a common glass encapsulated fuse, a trace fuse on a printed circuit board, or other similar structure that provides the function of a fuse. For example, a switch or switching circuit may be used to provide the functionality of fuse 375.

Power source 310 is typically a rechargeable battery with associated electronics. In other cases, power source 310 is a disposable battery or simply a connection to an independent power source, such as a switch mode power supply. In this embodiment, power source 310 also includes the charging and current driving electronics associated with it.

Controller 305 is typically an integrated circuit with power, input, and output pins capable of performing logic functions. In various embodiments, controller 305 is a targeted device controller. In such a case, controller 305 performs specific control functions targeted to a specific device or component, such as a heater or a power supply. For example, a heater controller has the basic functionality to control a heater. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. In the embodiment of FIG. 3, controller 305 controls power supply 310 and reads data from memory device 315. While depicted as one component in FIG. 1, controller 305 may be made of many different components or integrated circuits.

Figure 8:
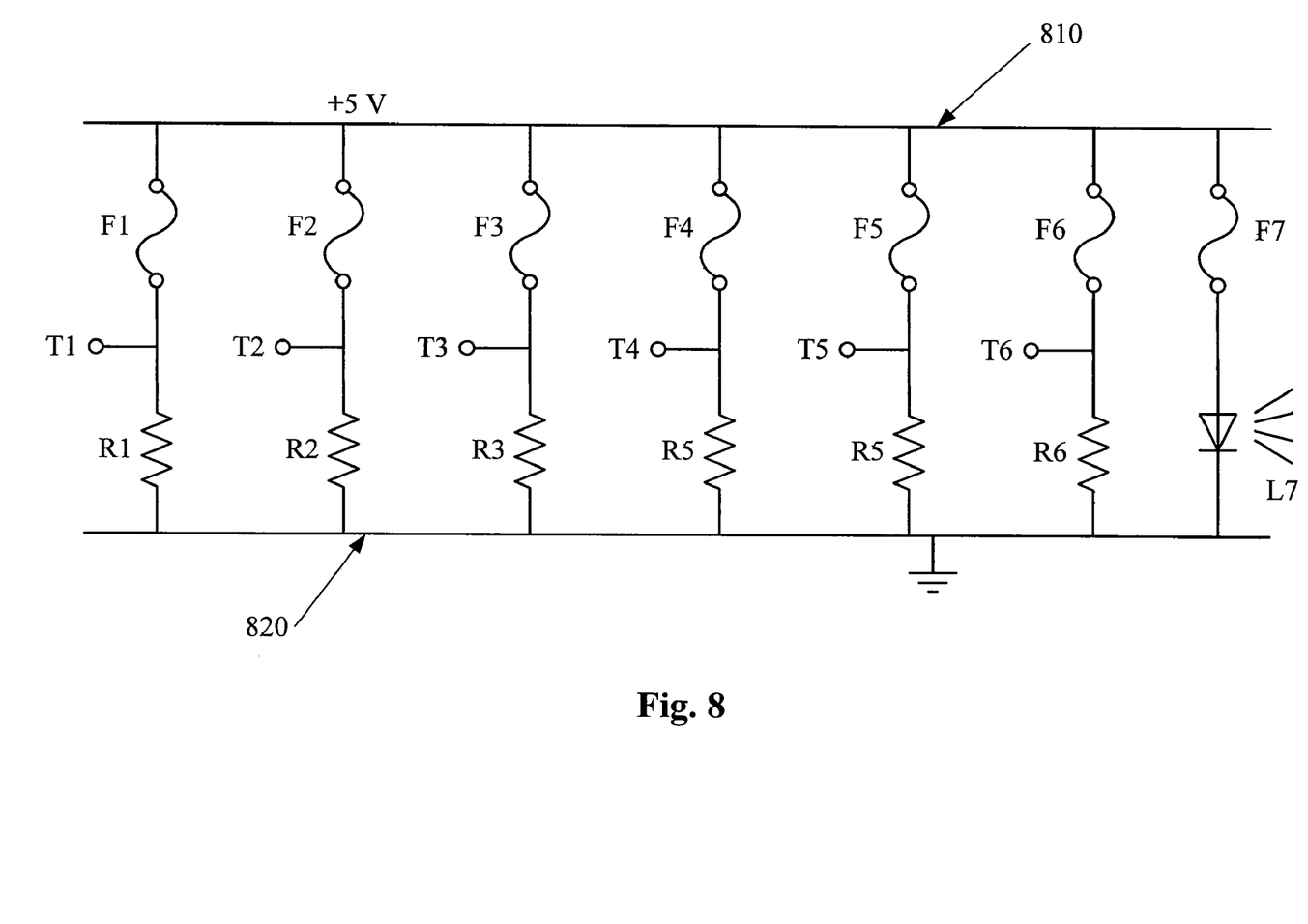
FIG. 8 is a circuit diagram of a hard-wired memory circuit according to an embodiment of the present invention.

Memory device 315 is a hard wired memory device such as that described in FIG. 8. Unlike a typical semiconductor memory, such as an EEPROM or flash memory, which cannot withstand gamma sterilization without data loss, memory device 315 withstands gamma sterilization without data loss. Memory device 315 is typically packaged with a disposable tip segment or drug delivery device. Such a package is sterilized before leaving the factory. In order to preserve the data stored on memory device 315, memory device 315 is hard-wired or resistant to commonly used sterilization techniques, such as gamma sterilization.

Figure 4:
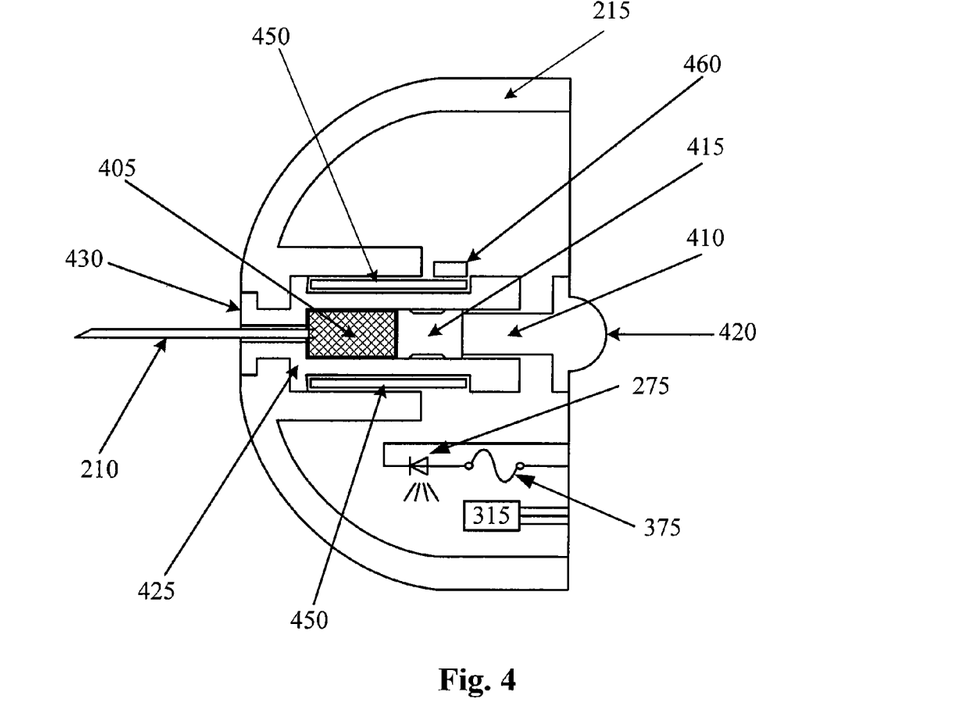
FIG. 4 is an exploded cross section view of a drug delivery tip segment for an ophthalmic hand piece according to an embodiment of the present invention.

FIG. 4 is an exploded cross section view of a drug delivery tip segment for an ophthalmic hand piece according to an embodiment of the present invention. In FIG. 4, the drug delivery tip segment includes housing 215, needle 210, optional light 275, fuse 375, memory device 315, plunger shaft 410, plunger tip (or fluid seal) 415, mechanical linkage interface 420, dispensing chamber 405, dispensing chamber housing 425, heater 450, thermal sensor 460, and optional luer 430.

In the embodiment of FIG. 4, mechanical linkage interface is located on one end of plunger shaft 410. Plunger tip 415 is located on the other end of plunger shaft 410. Plunger shaft 410 and plunger tip 415 collectively form a plunger. Dispensing chamber 405 is enclosed by dispensing chamber housing 425 and plunger tip 415. Plunger tip 415 forms a fluid seal with the interior surface of dispensing chamber housing 425. Needle 210 is fluidly coupled to dispensing chamber 405. In this manner, a substance located in dispensing chamber 405 can be contacted by plunger tip 415 and pushed out of needle 210. Needle 210 may be secured to the drug delivery tip segment by an optional luer 430 or may be permanently attached. Heater 450 is located on dispensing chamber housing 425 and at least partially surrounds dispensing chamber 405. Housing 215 forms an outer skin on the drug delivery tip segment and at least partially encloses plunger shaft 410, plunger tip 415, dispensing chamber 405, and dispensing chamber housing 425.

A substance to be delivered into an eye, typically a drug, is located in dispensing chamber 405. In this manner, the substance is contacted by the inner surface of dispensing chamber housing 425 and one face of plunger tip 415. Typically, dispensing chamber 405 is cylindrical in shape. Heater 450 is in thermal contact with dispensing chamber housing 425. In this manner, heater 450 is adapted to heat the contents of dispensing chamber 425. Current is applied to heater 450 through an electrical interface (not shown). Thermal sensor 460 provides temperature information to assist in controlling the operation of heater 450.

In one embodiment of the present invention, the substance located in dispensing chamber 405 is a drug that is preloaded into the dispensing chamber. In such a case, the drug delivery tip segment is appropriate as a single use consumable product. Such a disposable product can be assembled at a factory with a dosage of a drug installed. A precise volume of a substance can be preloaded into the delivery device.

When the drug is preloaded into dispensing chamber 405, a set quantity of the drug can be preloaded. For example, 100 microliters of a drug can be loaded into dispensing chamber 405, and any quantity up to 100 microliters can be dispensed. In such a case, the plunger (plunger shaft 410 and plunger tip 415) can be moved a precise distance to deliver a precise dosage of drug from the dispensing chamber 405, through the needle 210, and into an eye. This provides for flexibility of dosing and for ease of assembly.

In other embodiments, different dosages may be preloaded into different tip segments. For example, dosages up to ten microliters in one microliter increments may be preloaded into dispensing chamber 405 of different tip segments. The proper dosage may be selected by selecting the tip segment with the proper amount of drug preloaded in dispensing chamber 405.

In operation, the drug delivery tip segment of FIG. 4 is attached to a limited reuse assembly (not shown). The limited reuse assembly provides power to the tip segment and illuminates optional light 275. In such a case, a current passes through optional light 275 and fuse 375. Mechanical linkage interface 420 mates with a mechanical interface on the limited reuse assembly. Dosage information is read from memory device 315. This dosage information enables the controller to operate the plunger such that the correct dosage is delivered. When a force is applied to plunger shaft 410, plunger tip 415 is displaced. The displacement of plunger tip 415 in turn displaces the substance contained in dispensing chamber 405. The substance is pushed out of needle 210. After the dosage is delivered, the controller (not shown) directs an increased current to be sent through fuse 375. This increased current burns out fuse 375 indicating that the tip segment has been used and is to be discarded. Since the tip segment of the depicted embodiment is a single use tip segment, once fuse 375 is blown, the tip segment is no longer operable. In addition, once fuse 375 is blown, data cannot be read from memory device 315.

Figure 5:
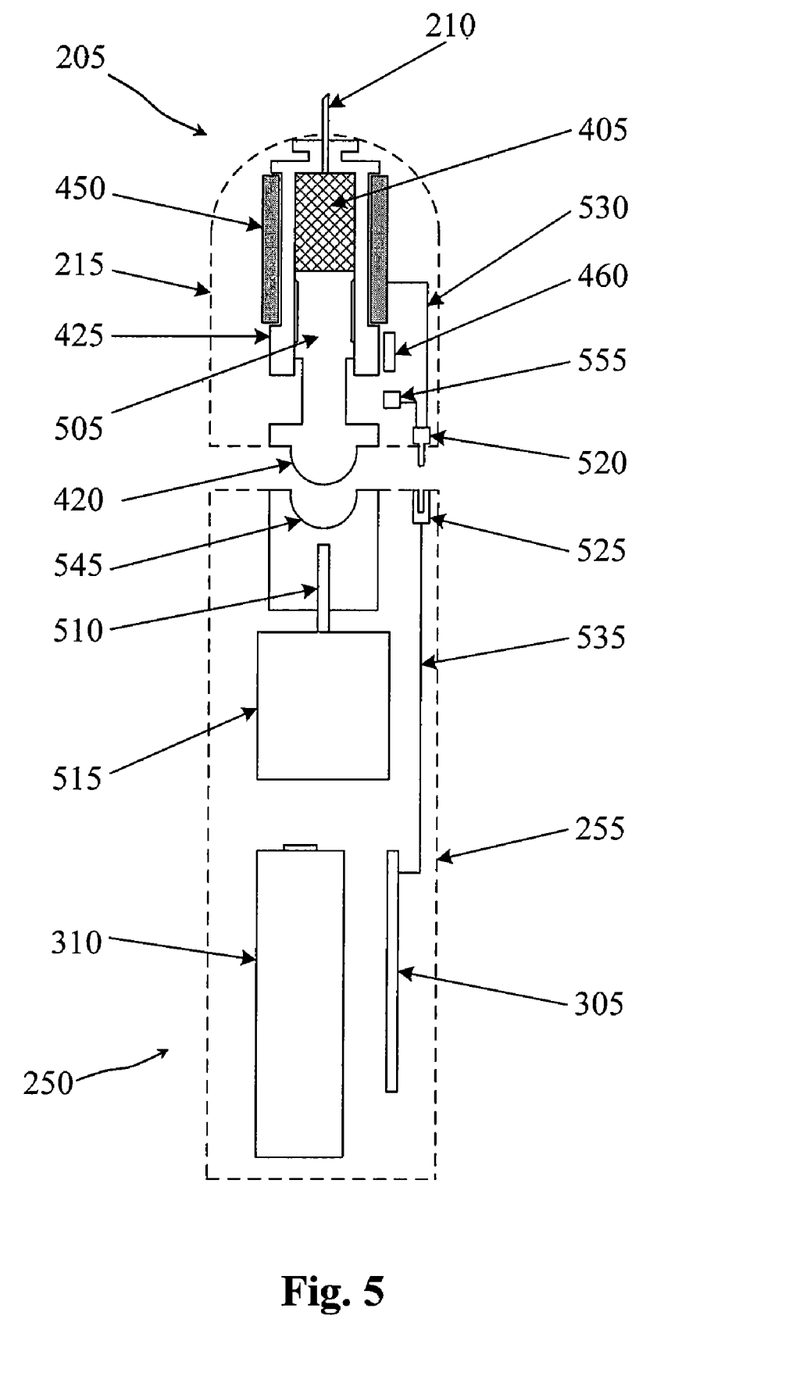
FIG. 5 is cross section view of a drug delivery tip segment and a limited reuse assembly according to an embodiment of the present invention.

FIG. 5 is a cross section view of a drug delivery tip segment and a limited reuse assembly according to an embodiment of the present invention. FIG. 5 shows how tip segment 205 interfaces with limited reuse assembly 250. In the embodiment of FIG. 5, tip segment 205 includes memory assembly 555, mechanical linkage interface 420, plunger 505, dispensing chamber housing 425, tip segment housing 215, heater 450, thermal sensor 460, needle 210, dispensing chamber 405, interface 530, and tip interface connector 520. Limited reuse assembly 250 includes mechanical linkage 545, actuator shaft 510, actuator 515, power source 310, controller 305, limited reuse assembly housing 255, interface 535, and limited reuse assembly interface connector 525.

In tip segment 205, mechanical linkage 420 is located on one end of plunger 505. The other end of plunger 505 forms one end of dispensing chamber 405. Plunger 505 is adapted to slide within dispensing chamber 405. An outer surface of plunger 505 is fluidly sealed to the inner surface of dispensing chamber housing 425. Dispensing chamber housing 425 surrounds the dispensing chamber 405. Typically, dispensing chamber housing 425 has a cylindrical shape. As such, dispensing chamber 405 also has a cylindrical shape.

Needle 210 is fluidly coupled to dispensing chamber 405. In such a case, a substance contained in dispensing chamber 405 can pass through needle 210 and into an eye. Heater 450 at least partially surrounds dispensing chamber housing 425. In this case, heater 450 is adapted to heat dispensing chamber housing 425 and any substance contained in dispensing chamber 405. In other words, heater 450 is in thermal contact with dispensing chamber housing 425. Interface 530 connects heater 450 with tip interface connector 520.

The components of tip segment 205, including dispensing chamber housing 425, heater 450, and plunger 505 are at least partially enclosed by tip segment housing 215. In one embodiment consistent with the principles of the present invention, a seal is present on a bottom surface of tip segment housing 215. In this manner, plunger 505 is sealed to tip segment housing 215. This seal prevents contamination of any substance contained in dispensing chamber 405. For medical purposes, such a seal is desirable. This seal can be located at any point on plunger 505 or on dispensing chamber housing 425. In such a case, tip segment housing 215 maybe connected to dispensing chamber housing 425 to form an air tight or fluid tight seal. In another embodiment, tip segment housing 215 maybe sealed to plunger 505 near the end on which mechanical linkage interface 420 resides. In such a case, an air tight or fluid tight seal may be formed between a location on plunger 505 and tip segment housing 215.

In addition, tip segment 205 may contain a plunger stop mechanism. As shown in FIG. 5, the bottom portion of plunger 505 (the portion on which mechanical linkage interface 420 resides) is adapted to contact the bottom portion of dispensing chamber housing 425. In such a case, as plunger 505 advances upward toward needle 210, mechanical linkage interface 420 also advances upward toward needle 210. A top surface of mechanical linkage interface 420 contacts a bottom surface of dispensing chamber housing 425. In this embodiment, the protrusions on the bottom end on plunger 505 and the bottom surface of dispensing chamber housing 425 form a plunger stop mechanism. Plunger 505 cannot be advanced any further than the point at which the top surface of mechanical linkage interface 420 contacts the bottom surface of dispensing chamber housing 505. Such a plunger stop mechanism can provide a safety feature, such as to prevent plunger 505 from contacting needle 210 and possibly dislodging it. In another embodiment consistent with the principles of the present invention, such a plunger stop mechanism may also include a locking mechanism so that plunger 505 cannot be retracted or moved away from needle 210 when needle 210 is removed from the eye. Such a plunger lock mechanism helps to prevent reflux of the substance when needle 210 is removed.

In limited reuse assembly 250, power source 310 provides power to actuator 515. An interface (not shown) via the controller 305 connects the power source 310 to the actuator 515. Actuator 515 is connected to actuator shaft 510. When actuator 515 is a stepper motor, actuator shaft 510 is integral with actuator 515. Mechanical linkage interface 545 is connected to actuator shaft 510. In this configuration, as actuator 515 moves actuator shaft 510 upward toward needle 210 mechanical linkage 545 also moves upward toward needle 210.

Controller 305 is connected via interface 535 to limited reuse assembly interface connecter 525. Limited reuse assembly interface connecter 525 is located on a top surface of limited reuse assembly housing 255 adjacent to mechanical linkage interface 545. In this manner, both limited reuse assembly interface connector 525 and mechanical linkage interface 545 are adapted to be connected with tip interface connector 520 and mechanical linkage interface 420 respectively.

Controller 305 and actuator 515 are connected by an interface (not shown). This interface (not shown) allows controller 305 to control the operation of actuator 515. The controller 305 has the ability to interface with either a rechargeable or non rechargeable power source 310. Controller 305 may control the current or voltage provided to memory assembly 555, for example, to illuminate an optional light 275 and blow a fuse 375 contained within memory assembly 555.

Tip segment 205 is adapted to mate with or attach to limited reuse assembly 250 as previously described. In the embodiment of FIG. 5, mechanical linkage interface 420 located on a bottom surface of plunger 505 is adapted to connect with mechanical linkage interface 545 located near a top surface of limited reuse assembly housing 255. In addition, tip interface connector 520 is adapted to connect with limited reuse assembly interface connector 525. When tip segment 205 is connected to limited reuse assembly 250 in this manner, actuator 515 and actuator shaft 510 are adapted to drive plunger 505 upward toward needle 210. In addition, an interface is formed between controller 305 and heater 450. A signal can pass from controller 305 to heater 450 through interface 535, limited reuse assembly interface connector 525, tip interface connector 520, and heater interface 530.

In operation, when tip segment 205 is connected to limited reuse assembly 250, controller 305 controls the operation of actuator 515. Actuator 515 is actuated and actuator shaft 510 is moved upward toward needle 210. In turn, mechanical linkage interface 545, which is connected to mechanical linkage interface 420, moves plunger 505 upward toward needle 210. A substance located in dispensing chamber 405 is then expelled through needle 210.

In addition, controller 305 controls the operation of heater 450. Heater 450 is adapted to heat an outside surface of dispensing chamber housing 425. Since dispensing chamber housing 425 is at least partially thermally conductive, heating dispensing chamber housing 425 heats a substance located in dispensing chamber 405. Temperature information can be transferred from thermal sensor 460 through interface 530, tip interface connector 520, limited reuse assembly interface connector 525, and interface 535 back to controller 305. This temperature information can be used to control the operation of heater 450. Typically, controller 305 controls the amount of current that is sent to heater 450. The more current sent to heater 450, the hotter it gets. In such a manner, controller 305 can use a feed back loop utilizing information from thermal sensor 460 to control the operation of heater 450. Any suitable type of control algorithm, such as a proportional integral derivative (PID) algorithm, can be used to control the operation of heater 450.

Memory assembly 555 is connected to interface 530 in tip segment 205. In the present embodiment, memory assembly 555 includes optional light 275, fuse 375, and memory device 315 as described with respect to FIGS. 3 and 4. The memory device 315 in memory assembly 555 is typically a hard wired memory circuit like that depicted in FIG. 8. The memory device 315 in memory assembly 555 is configured to store dosage information for a drug contained in dispensing chamber 405.

Controller 305 is also adapted to interface with memory assembly 555. In this manner, controller 305 directs current to flow from power source 310 to memory assembly 555. Controller 305 also reads data from the memory device contained in memory assembly 555. A current passing through optional light 275 and fuse 375 illuminates optional light 275. After the tip segment 205 has been used (after the substance has been dispensed), controller 305 directs power source 310 to deliver an increased current to blow fuse 375 and extinguish optional light 275. This indicates that the tip segment 205 has been used and that it should be discarded. In addition, controller 305 may check fuse 375 to see if it is blown. If it is blown, controller 305 defines tip segment 205 as rendered inoperable. Alternatively, fuse 375 may be placed such that when it is blown, no power is delivered to the tip segment. In such a case, once fuse 375 is blown, optional light 275 is extinguished and the tip segment is rendered inoperable. In addition, once fuse 375 is blown, data may no longer be read from the memory device in memory assembly 555.

In the embodiment of FIG. 5, interface 530, tip interface connector 520, limited reuse assembly interface 525, and interface 535 all form a data interface between tip segment 205 and limited reuse assembly 250. In this manner, information from the thermal sensor 460 maybe passed back to limited reuse assembly 250 via this series of interfaces and interface connectors. In addition, data stored on the memory device in memory assembly 555 may also be read by controller 305 via this series of interfaces and interface connectors. When tip segment 205 is connected to limited reuse assembly 250, mechanical linkage interface 545 is connected to mechanical linkage interface 420 and tip interface connector 520 is connected to limited reuse assembly interface connector 525. The connection of tip interface connector 520 to limited reuse assembly interface connector 525 allows the transfer of information or data from thermal sensor 460 and the memory device in memory assembly 555 to controller 305.

In one embodiment consistent with the principle of the present invention, the memory device in memory assembly 555 stores dosage information. Information about a proper drug dosage for a drug contained in dispensing chamber 405 is stored in the memory device in memory assembly 555. In such a case, controller 305 can read the dosage information from the memory device in memory assembly 555 and operate actuator 515 in a manner suitable to deliver the proper dosage. For example, 100 microliters may be contained dispensing chamber 405. Information stating that a dosage of 20 microliters is to be delivered into an eye maybe stored on the memory device in memory assembly 555. In such a case, controller 305 reads the dosage information (that 20 microliters should be delivered into the eye) from the memory device in memory assembly 555. Controller 305 can then operate actuator 515 to deliver the 20 microliter dosage. Controller 305 can cause actuator 515 to move actuator shaft 510 and mechanical linkage 545 a set distance related to a dosage of 20 microliters. In such a case, plunger 505 is moved this set distance so that only 20 micro liters of a drug is expelled from needle 210 and into an eye.

In one embodiment consistent with the principles of the present invention, controller 305 has various plunger distances stored on it. Each of these plunger distances is related to a different dosage. For example, one plunger distance may be associated with a dosage of 20 microliters and a second larger plunger distance may be associated with a dosage of 40 microliters. In this manner controller 305 can use the set plunger distance to control actuator 515, actuator shaft 510, mechanical linkage interface 545, and mechanical linkage interface 420 to move plunger 505 this set distance. In other words, controller 305 reads dosage information from the memory device in memory assembly 555, finds the plunger distance associated with that dosage, and uses the distance that plunger 505 must travel to deliver a given dosage of drug. Since actuator shaft 510 and mechanical linkage interface 545 are connected to mechanical linkage interface 420, a movement of actuator shaft 510 produces a corresponding movement of plunger 505. When actuator 515 is a stepper motor, controller 305 controls the movement of actuator 515 such that plunger 505 is moved the proper distance to deliver the required dosage from dispensing chamber 405, through needle 210, and into an eye.

In another embodiment consistent with the principles of the present invention, controller 305 may calculate a distance that plunger 505 must be moved to deliver the desired dosage. For example, if dosage information corresponding to a drug dosage of 20 microliters is read from the memory device in memory assembly 555 by controller 305, then controller 305 may use this information to calculate a proper distance that plunger 505 must be moved. Since the volume of dispensing chamber 405 as well as the volume of a drug loaded in dispensing chamber 405 is known, a distance that plunger 505 must be moved to deliver that required dosage can be calculated by controller 305. When dispensing chamber 405 has a cylindrical shape, the volume of the dispensing chamber can be calculated by using the cross section area of the cylinder (the area of a circle) times the height of the dispensing chamber. This simple mathematical formula can be used to calculate the total volume of the dispensing chamber 405. Since the cross section area of dispensing chamber 405 is constant for any given application, the height which corresponds to a distance that plunger 505 travels can be calculated for any dosage amount.

For example, assume that 100 microliters of a drug is loaded into dispensing chamber 405 and that the cross section area of dispensing chamber 405 is 10. When dispensing chamber 405 is in the shape of a cylinder, the height of that cylinder is also 10. To deliver a dosage of 20 microliters which corresponds to 20% of the total volume of dispensing chamber 405, it is necessary to move plunger 505 upward toward needle 210 a distance of 2. In other words, a dosage of 20 microliters corresponds to 20% of the total volume of dispensing chamber 405. In such a case, plunger 505 should be moved upward toward needle 210 a distance equal to 20% of the total height of dispensing chamber 405. Controller 305 can then control actuator 515 such that actuator shaft 510 moves drives plunger 505 upward a distance of 20% of the total height of dispensing chamber 405.

In addition, controller 305 may read information about a rate at which plunger 505 should be moved in order to properly deliver a dosage of drug. In such a case, controller 305 reads information about the rate of drug delivery from memory assembly 555 and uses that information to operate actuator 515 to drive plunger 505 at that rate. The rate at which plunger 505 moves may be fixed or variable. In some applications, it may be desirable to move plunger 505 faster than in other applications. For example, when the drug contained in dispensing 405 is a drug that should be heated before being injected into an eye, it may be desirable to drive plunger 505 at a rate such that the heated drug does not cool and clog needle 210. In other applications, it may be desirable to move plunger 505 slowly in order to improve the delivery of a drug contained in dispensing chamber 405.

Figure 6:
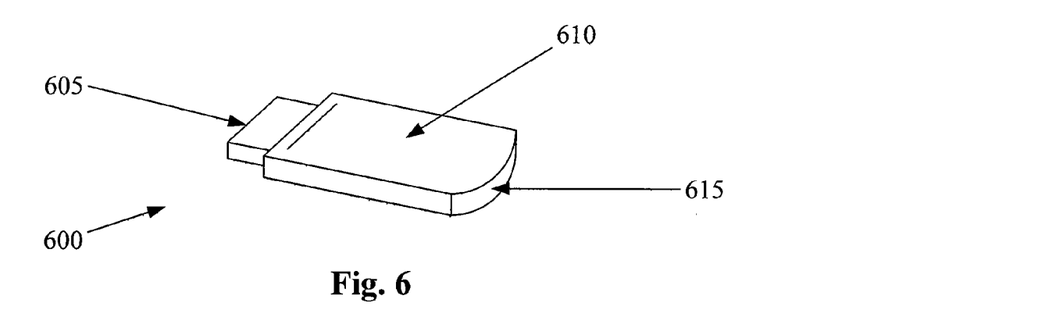
FIG. 6 is a perspective view of a dosage control card according to an embodiment of the present invention.

It is also desirable to include dosage information on the memory device in memory assembly 555 so that a dosing error is less likely to occur. In such a case, a number of different drug delivery tip segments 205 maybe manufactured and loaded with a drug at the factory. Dosage information can also be loaded onto the memory device in memory assembly 555 at the factory. A number of different tip segments, each with the same amount of drug contained in the dispensing chamber 405 but with different dosage information stored on the memory device in memory assembly 555, can be manufactured and shipped. Alternatively, a number of different tip segments, each with a different amount of drug contained in the dispensing chamber 405 with corresponding dosage information stored on the memory device in memory assembly 555, can be manufactured and shipped. A doctor can then order the tip segment 205 with the required dosage information on the memory device in memory assembly 555. Packaging can be clearly labeled to identify the dosage information so that the proper dosage is administered to a patient. Where memory assembly 555 is located on a separate card 600, that card 600 can be included with the drug delivery device 405.

FIG. 6 is a perspective view of a dosage control card according to an embodiment of the present invention. In the embodiment of FIG. 6, dosage control device 600 is implemented in a memory card-type device. The same structure and functionality previously described with respect to memory assembly 555 of FIG. 5 is implemented in dosage control device 600. Dosage control device 600 contains a fuse, light, and memory device (not shown) as previously described. Dosage control device 600 has a connector end 605, a body 610, and a lighted end 615. In this embodiment, the connector end 605 is adapted to connect to and allow communication with a console box 700. A light 275 is incorporated in lighted end 615.

Figure 7:
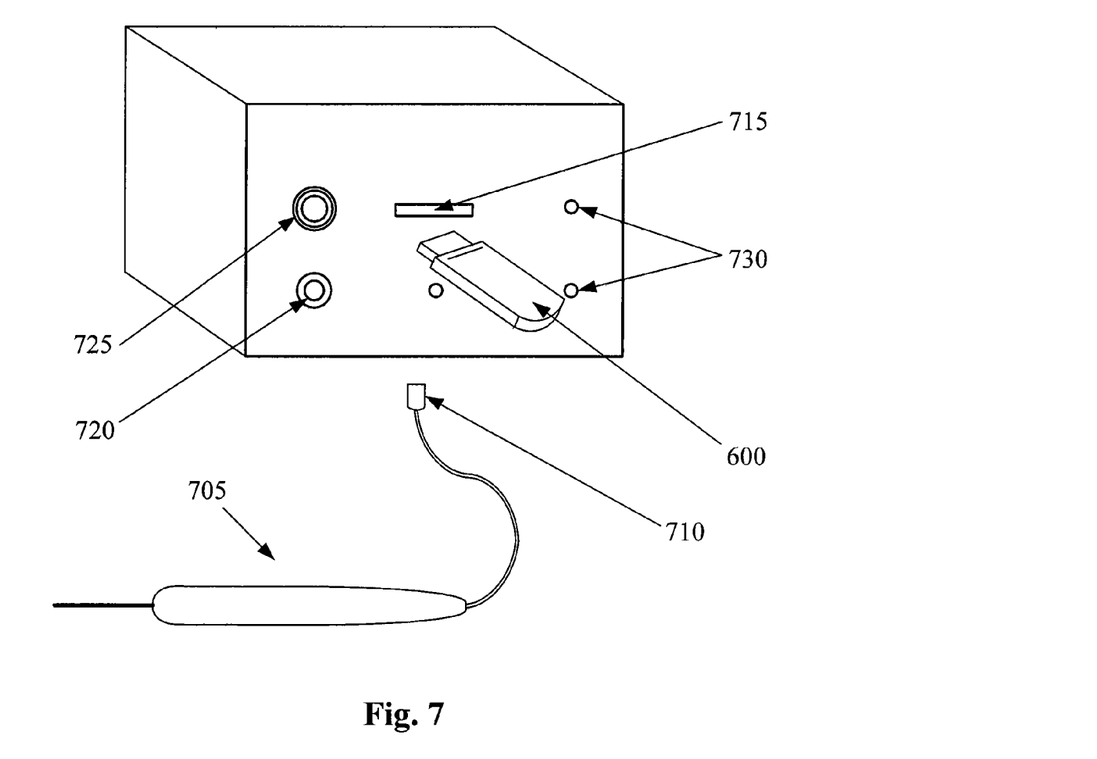
FIG. 7 is a perspective view of a console, a drug delivery device, and a dosage control card according to an embodiment of the present invention.

FIG. 7 is a perspective view of a console, a drug delivery device, and a dosage control card according to an embodiment of the present invention. In FIG. 7, console box 700 includes a slot 715, a port 720, a button 725, and indicators 730. Slot 715 is adapted to receive the connector end 605 of dosage control card 600. An injection device 705 has a connector 710. Port 720 is adapted to receive connector 710. Console box 700 includes a controller (not shown) that controls the operation of injection device 705. Injection device 705 includes the components of the embodiment shown in FIG. 5 with the exception of the power source, the controller, and possibly several indicators or lights. Those components are contained in the console box 700. In addition, the heater is optional, as it is optional in the previously described devices.

In operation, a medical professional removes injection device 705 and dosage control device 600 from sterilized packaging (not shown). The injection device 705 is connected to the console box 700 by connecting connector 710 to port 720. Dosage control device 600 is inserted into slot 715. The controller (not shown) in console box 700 reads the dosage information from the memory device on dosage control device 600. The controller in console box 700 then operates the injection device 705 to deliver the appropriate dosage in the manner previously described.

FIG. 8 is a circuit diagram of a hard wired memory circuit according to an embodiment of the present invention. In this embodiment, seven fuses (F1, F2, F3, F4, F5, F6, and F7), six resistors (R1, R2, R3, R4, R5, and R6), and one LED (L7) serve to store dosage data. The embodiment of FIG. 8 also includes six terminals (T1, T2, T3, T4, T5, and T6), a voltage line 810, and a ground line 820. Fuse F7 and LED L7 correspond to fuse 375 and optional light 275 in FIGS. 3 and 4.

The embodiment of FIG. 8 is capable of storing a five bit number and a checksum. As is commonly known, a voltage applied to voltage line 810 can be read across each of the six resistors. If the fuse in series with a particular resistor is blown, then no voltage will be read across that resistor. These two states (the presence or absence of a voltage across a resistor) correspond to a one or a zero in a binary number. In the embodiment of FIG. 8, five of the resistors contain dosage data. This dosage data is one of 32 distinct numbers. The sixth resistor holds checksum information.

For example, if fuses F2 and F3 are blown and fuses F1, F4, F5, and F6 are not blown, then no voltage (or a zero voltage) will be present across resistors R2 and R3 and a full voltage (+5 volts) will be present across resistors R1, R4, R5, and R6. In this example, the five bits correspond to the first five resistors (R1-R5), and the checksum corresponds to the sixth resistor (R6). The voltage across each resistor is read between the respective terminal (T1-T6) and the ground line 820. In this case, the five bit binary number is 10011 or 19, and the checksum is 1. The controller reads this number and the checksum, determines if the number is correct in light of the checksum, and then determines a dosage based on the number. In this case, the dosage control device defines 32 different dosage levels. The number 19 could correspond to a dosage of 48 microliters. In such a case, dosages from 10 to 72 microliters in two microliter increments can be defined by the dosage control device. The controller can then operate the plunger to deliver 48 microliters. After the dosage is delivered, a fuse can be blown, and the card can be rendered inoperable, as previously described.

From the above, it may be appreciated that the present invention provides an improved system for delivering precise volumes of a substance into an eye. The present invention provides a drug delivery device that is capable of delivering a precise dosage. The tip segment interfaces with a universal hand piece limited reuse assembly. Information on the dosage control device directs the injection device to deliver the proper dosage. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An injection device comprising:
a dispensing chamber having an inner surface and an outer surface, the inner surface defining a cavity for receiving a quantity of a substance;
a plunger engaged with the inner surface of the dispensing chamber, the plunger capable of sliding in the cavity of the dispensing chamber, the plunger fluidly sealed to the inner surface of the dispensing chamber;
a controller for controlling the operation of the injection device;
a memory device resistant to sterilization techniques that would erase semiconductor memory, the memory device comprising a first resistor connected in series with a first fuse, a second resistor connected in series with a second fuse, and a voltage applied across the first and second fuse-resistor pairs, the memory device located in a disposable portion of the injection device, the memory device with preprogrammed dosage data; and
a housing at least partially enclosing the dispensing chamber and the plunger;
wherein the controller reads the dosage data from the memory device and operates the injection device to deliver a dosage corresponding to the dosage data.

2. The injection device of claim 1 further comprising:
a fuse, such that after the substance has been delivered from the dispensing chamber, the fuse is blown disabling the device.

3. The injection device of claim 1 further comprising:
a needle fluidly coupled to the dispensing chamber.

4. The injection device of claim 1 further comprising:
a heater in thermal contact with the dispensing chamber, the heater for heating the substance.

5. The injection device of claim 1 further comprising:
a plunger stop mechanism for limiting movement of the plunger.

6. The injection device of claim 1 wherein the substance is a drug for treating a condition of the eye.

7. The injection device of claim 2 further comprising a light in series with the fuse.

8. The injection device of claim 1 further comprising:
a power source for providing power to the injection device.

9. The injection device of claim 8 wherein the power source is a battery.

10. The injection device of claim 1 further comprising:
an actuator for driving the plunger.

11. An ophthalmic injection system comprising:
a tip segment and a limited reuse assembly;
the tip segment comprising:
a dispensing chamber having an inner surface and an outer surface, the inner surface defining a cavity for receiving a quantity of a substance;
a plunger engaged with the inner surface of the dispensing chamber, the plunger capable of sliding in the cavity of the dispensing chamber, the plunger fluidly sealed to the inner surface of the dispensing chamber, the plunger having a proximate end and a distal end; the proximate end having a first mechanical linkage interface;
a memory device resistant to sterilization techniques that would erase semiconductor memory, the memory device comprising a first resistor connected in series with a first fuse, a second resistor connected in series with a second fuse, and a voltage applied across the first and second fuse-resistor pairs, the memory device with preprogrammed dosage data; and
a first housing at least partially enclosing the dispensing chamber and the plunger;

the limited reuse assembly comprising:
a power source;
a controller for controlling the operation of the system;
a actuator having a shaft;
a second mechanical linkage interface located on an end of the shaft; and
a second housing at least partially enclosing the controller and the actuator;
wherein the controller reads the dosage data from the memory device and operates the injection device to deliver a dosage corresponding to the dosage data.

12. The system of claim 11 wherein the tip segment further comprises:
a fuse, such that after the substance has been delivered from the dispensing chamber, the fuse is blown disabling the device.

13. The system of claim 11 further comprising:
an interface for coupling the memory device to the controller.

14. The system of claim 11 wherein the controller operates the actuator such that the shaft is moved a calculated distance thereby displacing the plunger and causing an amount of the substance corresponding to the dosage data to exit the dispensing chamber.

15. The system of claim 11 further comprising:
a needle fluidly coupled to the dispensing chamber.

16. The system of claim 11 further comprising:
a heater in thermal contact with the dispensing chamber, the heater for heating the substance.

17. The system of claim 11 wherein the substance is a drug for treating a condition of the eye.

18. The system of claim 11 wherein the tip segment further comprises a light in series with the fuse.

19. The system of claim 11 wherein the power source is a battery.

* * * * *